(12) United States Patent
Royalty et al.

(10) Patent No.: US 8,202,527 B2
(45) Date of Patent: Jun. 19, 2012

(54) METHOD OF COMBATING TURF PESTS WITH A COMBINATION OF IMIDACLOPRID AND BIFENTHRIN

(75) Inventors: Reed Nathan Royalty, Cary, NC (US); Jeffrey A. Michel, Orlando, FL (US); Michael Anthony Ruizzo, Raleigh, NC (US)

(73) Assignee: Bayer CropScience LP, Research Triangle Park, NC (US)

( * ) Notice: Subject to any disclaimer, the term of this patent is extended or adjusted under 35 U.S.C. 154(b) by 206 days.

(21) Appl. No.: 11/886,618

(22) PCT Filed: Mar. 13, 2006

(86) PCT No.: PCT/US2006/008929
§ 371 (c)(1),
(2), (4) Date: Jan. 16, 2009

(87) PCT Pub. No.: WO2006/101805
PCT Pub. Date: Sep. 28, 2006

(65) Prior Publication Data
US 2009/0215832 A1    Aug. 27, 2009

Related U.S. Application Data

(63) Continuation-in-part of application No. 11/085,451, filed on Mar. 21, 2005, now abandoned.

(51) Int. Cl.
*A01N 25/32* (2006.01)
*A01N 25/12* (2006.01)
*A01N 43/40* (2006.01)
*A01N 53/12* (2006.01)

(52) U.S. Cl. ........ 424/406; 424/405; 424/409; 514/341; 514/531

(58) Field of Classification Search ............. None
See application file for complete search history.

(56) References Cited

U.S. PATENT DOCUMENTS 6,660,690 B2 * 12/2003 Asrar et al. ............. 504/100
2008/0319023 A1 * 12/2008 Richman et al. ........ 514/341

FOREIGN PATENT DOCUMENTS

WO     WO 2004048115    *   6/2002
WO     WO03015518       *   2/2003

OTHER PUBLICATIONS

Potter; Managing Insect Pests of Sports Fieldsacta Horticulurae # 661, pp. 449-461, 2004.*
Allectus Fact Sheet—Bayer ES Nov. 5, 2004.*
Allectus SC—Bayer—Mar. 2005.*

* cited by examiner

*Primary Examiner* — Neil Levy
(74) *Attorney, Agent, or Firm* — Andrew T. Prokopetz

(57) ABSTRACT

This invention relates to a method of controlling surface insect pests of turf using bifenthrin and imidacloprid.

8 Claims, 2 Drawing Sheets

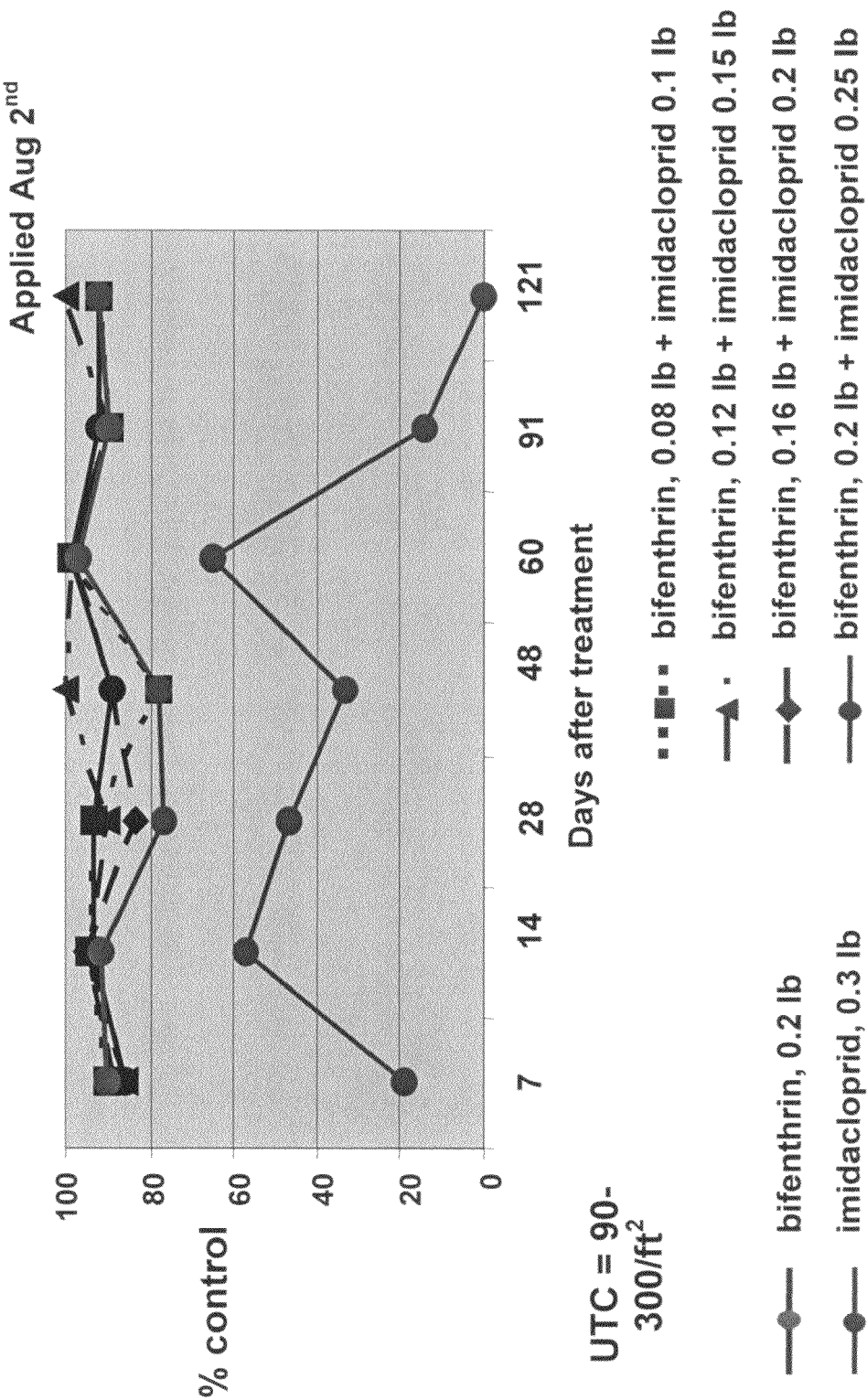

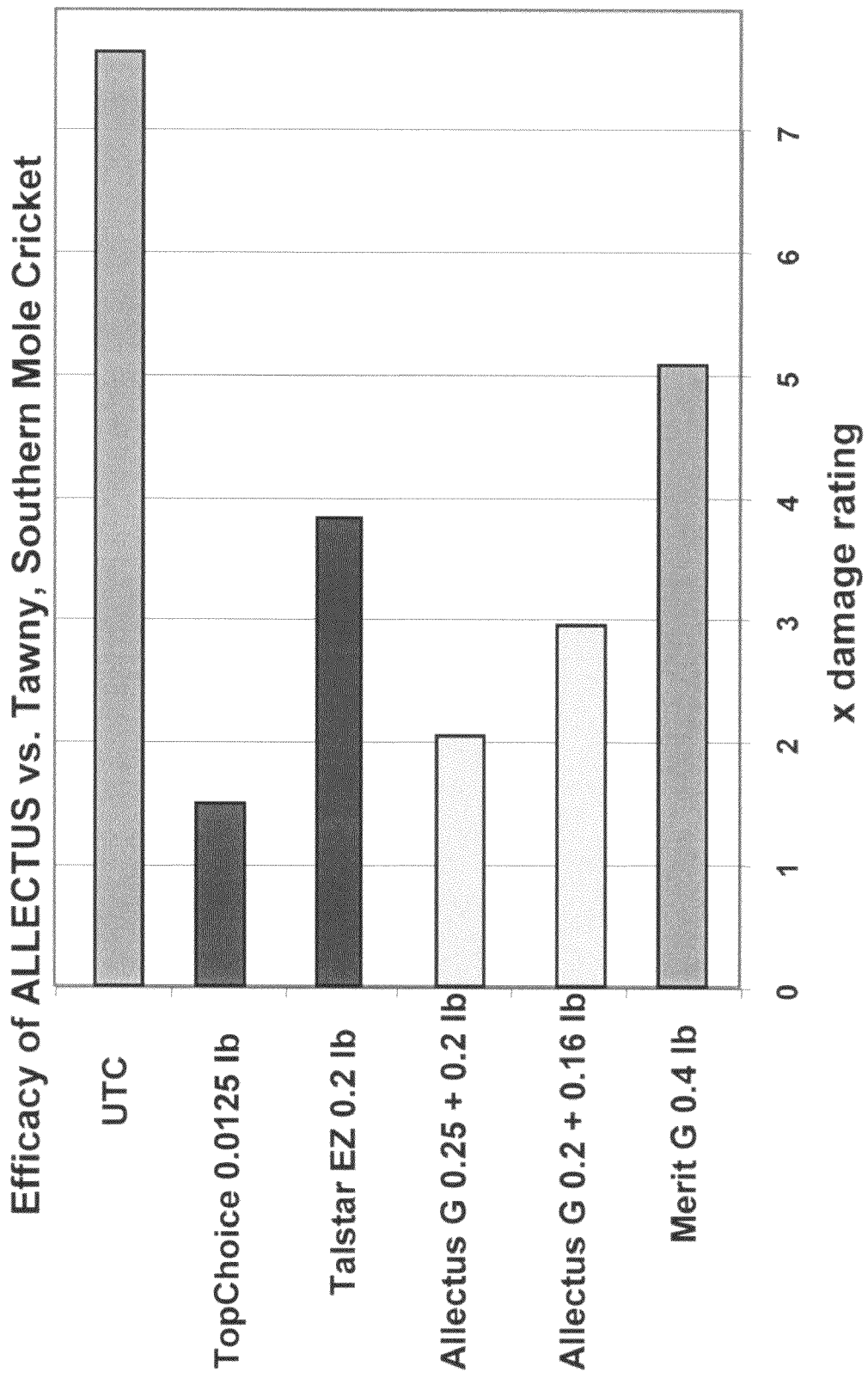

METHOD OF COMBATING TURF PESTS WITH A COMBINATION OF IMIDACLOPRID AND BIFENTHRIN

CROSS REFERENCE TO RELATED APPLICATIONS

This application is a National Stage Application of PCT/US2006/008929, filed Mar. 13, 2006, and is a Continuation-in-Part of U.S. patent application Ser. No. 11/085,451, filed Mar. 21, 2005 now abandoned. The contents of each of these applications is hereby incorporated by reference in their entireties.

BACKGROUND OF THE INVENTION

The present invention relates to the control of turf pests at a locus, particularly a turfgrass locus.

Imidacloprid is an insecticide known to the skilled artisan to control a variety of pests. U.S. Pat. No. 4,742,060 provides a description of imidacloprid and some uses. Imidacloprid is known to control some turf pests, for example, the larvae of *Popillia japonica* Newm.

Bifenthrin is an insecticide known to the skilled artisan to control a variety of pests. Bifenthrin is generally known as 2-methylbiphenyl-3-ylmethyl (Z)-(1RS,3RS)-3-(2-chloro-3,3,3-trifluoroprop-1-enyl)-2,2-dimethylcyclopropane-carboxylate, CAS Registry Number 82657-04-3. Bifenthrin is described in *The Pesticide Manual*, page 88 (entry 76), C. D. S. Thomas, ed. (13$^{th}$ Ed., 2003).

Bifenthrin is known to provide some control of Hemepteran insects of the family Lygaeidae, particularly those known to the skilled artisan as chinch bugs, big-eyed bugs or false chinch bugs. However, the length of control of chinch bugs, particularly the southern chinch bug, *Blissus insularis*, using bifenthrin may not be completely satisfactory at application rates below about 0.2 lb AI/A (about 220 g/ha). Furthermore, widespread use of bifenthrin for management of chinch bugs has resulted in the development of widespread resistance to this active ingredient.

An object of the present invention is to provide a new method of controlling some lawn pests, including chinch bugs. Another object of the present invention is to provide a new composition of insecticides to control some lawn pests, including chinch bugs. Another object of the present invention is to provide control of pesticide-resistant lawn pests, especially chinch bugs. These and other objects of the invention are met in whole or in part by the means of the present invention.

SUMMARY OF THE INVENTION

The present invention provides a method of controlling insect pests (particularly chinch bugs and cricket moles) in turfgrass comprising applying a composition comprising a synergistically effective amount of imidacloprid and bifenthrin to turf that is susceptible to damage by insect pests.

The present invention also provides a method of controlling surface feeding insect pests in turf grass in need of pest control comprising applying a composition comprising bifenthrin and imidacloprid at a rate at which one application of the composition provides control that is substantially biologically equivalent to 1.8 to 2.5 applications of bifenthrin when used alone at the same rate at which bifenthrin is used in the single application of the combination. In general, it is possible to apply less imidacloprid in the combinations of the invention than when used alone, while at the same time obtaining greater efficacy.

The present invention also provides a composition comprising a synergistically effective amount of imidacloprid and bifenthrin which in use controls insect pests, particularly chinch bugs, in turfgrass. The composition also consists of synergistically effective amounts of imidacloprid and bifenthrin that controls pyrethroid-resistant chinch bugs in turfgrass.

The present invention also provides a product for the control of chinch bugs which comprises the separate, sequential or simultaneous application of imidacloprid and bifenthrin.

BRIEF DESCRIPTION OF THE DRAWINGS

FIG. 1 shows test results showing the effectiveness of a soluble composition according to Example 1 on chinch bugs.

FIG. 2 shows test results showing the effectiveness of a granular composition according to Example 1 on southern and tawny mole crickets.

DETAILED DESCRIPTION OF THE INVENTION

Generally, imidacloprid and bifenthrin are admixed to form the composition. The composition may be a solid or liquid composition according to the knowledge of the skilled artisan. Examples of suitable compositions include granules, dusts, powders, and wettable powders. Suitable liquids include emulsifiable concentrates, solutions, flowables, suspension concentrates and suspensions.

The amount of active ingredients in the composition of the invention can vary widely but is generally from about 0.1% to about 95% of active ingredient. (Percents are generally percent by weight in the current specification and claims of the present application unless otherwise denoted.) Preferably, the ratio of the amount of bifenthrin to the amount of imidacloprid is from about 1:5 to about 4:6. The amount of bifenthrin and imidacloprid in a soluble concentrate formulation varies from about 2% to about 4% and from about 4% to about 5%, respectively. The amount of bifenthrin and imidacloprid in granular formulations varies from about 0.1 to about 0.2% and from about 0.125 to about 0.25%, respectively.

The remainder of the composition up to 100% comprises a carrier as well as various additives such as those hereafter indicated. By "carrier", there is meant herein an organic or inorganic material, which can be natural or synthetic and which is associated with the active ingredient and which facilitates its application to the locus to be treated or crop. This carrier is thus generally inert and should be agriculturally acceptable, especially on the contemplated or treated locus or crop. The carrier can be solid (for example, clay, silicates, silica, resins, wax, fertilizers, or the like) or liquid (for example, water, alcohols, ketones, oil solvents, saturated or unsaturated hydrocarbons, chlorinated hydrocarbons, liquified petroleum gas, or the like).

Among the many additives, the compositions of the invention can comprise surfactants as well as other ingredients such as dispersants, stickers, antifoam agents, antifreezing agents, dyestuffs, thickeners, adhesives, protective colloids, penetrating agents, stabilizing agents, sequestering agents, antiflocculating agents, corrosion inhibitors, pigments and polymers.

More generally, the compositions of the invention can comprise all kinds of solid or liquid additives which are known in the art of insecticides and insecticidal treatments.

The surfactants can be of the emulsifying or wetting type, ionic or non-ionic. Possible surfactants are salts of polyacrylic or lignosulfonic acids; salts of phenolsulfonic or naphthalenesulfonic acids; poly-condensates of ethylene oxide with fatty alcohols or fatty acids or fatty amines or substituted phenols (particularly alkylphenols or arylphenols); ester-salts of sulfosuccinic acids; taurine derivatives, such as alkyl taurates; phosphoric esters; or esters of alcohols or polyoxyethylated phenols. When the spraying vehicle is water, the use of at least one surfactant is generally employed.

Imidacloprid is generally used alone at a rate of from about 0.3 to about 0.4 lb/A (about 340 to about 450 g/ha) and bifenthrin is generally used alone at a rate of from about 0.1 to about 0.2 lb/A (about 110 to about 220 g/ha) to control mole crickets. Both active ingredients must be applied during peak egg hatch to be effective, and even then the control obtained is inconsistent and often not commercially acceptable.

Therefore, for compositions according to the invention, imidacloprid is generally used at a rate of from about 200 to about 560 g/ha (preferably from 200 to 350 g/ha) and bifenthrin is generally used at a rate of from about 85 to about 450 g/ha (preferably 150 to 450 g/ha, more preferably 150 to 250 g/ha) to control mole crickets. At these doses, control provided by both imidacloprid and bifenthrin alone often is insufficient and is inconsistent.

Imidacloprid alone is generally used at a rate of from about 0.3 to about 0.4 lb/A (about 340 to about 450 g/ha) to control chinch bugs, but with poor efficacy. Bifenthrin alone is used at a rate of from about 0.1 to about 0.2 lb/A (about 110 to about 220 g/ha) to control chinch bugs. Doses of bifenthrin below 0.1 to about 0.2 lb/A (about 110 to about 220 g/ha) are often ineffective, especially against pyrethroid-resistant chinch bugs.

Therefore, for compositions according to the invention, imidacloprid is generally used at a rate of from about 75 to about 560 g/ha (preferably from 150 to 300 g/ha, more preferably from 160 to 200 g/ha) and bifenthrin is generally used at a rate of from about 40 to about 450 g/ha (preferably from 56 to 220 g/ha, more preferably from 60 to 150 g/ha) to control chinch bugs. In a particularly preferred combination, imidacloprid is used at a rate of about 280 g/ha and bifenthrin is used at a rate of about 220 g/ha. At these doses, the efficacy of imidacloprid alone is inconsistent, particularly against southern chinch bug (*Blissus insularis*) At these doses of bifenthrin alone, control of southern chinch bug is sometimes insufficient and inconsistent.

Imidacloprid alone can used at a rate of from about 0.2 to about 0.5 lb/A (about 200 to about 560 g/ha) to control Japanese beetles (*Popillia japonica*) but bifenthrin alone is not effective in control Japanese beetles. However, compositions according to the invention using imidacloprid at a rate of from about 110 g/ha to about 1.1 kg/ha (preferably from 220 to 450 g/ha) and bifenthrin a rate of from about 45 to about 880 g/ha (preferably from 88 to 360 g/ha) are particularly effective in controlling Japanese beetles.

The present invention can be practiced with all turfgrasses, including cool season turfgrasses and warm season turfgrasses. Examples of cool season turfgrasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass, (*Poa glaucantha* Gaudin), wood bluegrass (*Poa nemoralis* L.), and bulbous bluegrass (*Poa bulbosa* L.); the bentgrasses and redtop (*Agrostis* spp.), such as creeping bentgrass (*Agrostis palustris* Huds.), colonial bentgrass (*Agrostis tenuis* Sibth.), velvet bentgrass (*Agrostis canina* L.), South German Mixed Bentgrass (*Agrostis* spp. including *Agrostis tenius* Sibth., *Agrostis canina* L., and *Agrostis palustris* Huds.), and redtop (*Agrostis alba* L.); the fescues (*Festucu* spp.), such as red fescue (*Festuca rubra* L. spp. *rubra*), creeping fescue (*Festuca rubra* L.), chewings fescue (*Festuca rubra commutata* Gaud.), sheep fescue (*Festuca ovina* L.), hard fescue (*Festuca longifolia* Thuill.), hair fescue (*Festucu capillata* Lam.), tall fescue (*Festuca arundinacea* Schreb.), meadow fescue (*Festuca elanor* L.); the ryegrasses (*Lolium* spp.), such as annual ryegrass (*Lolium multiflorum* Lam.), perennial ryegrass (*Lolium perenne* L.), italian ryegrass (*Lolium multiflorum* Lam.); and the wheatgrasses (*Agropyron* spp.), such as fairway wheatgrass (*Agropyron cristatum* (L.) Gaertn.), crested wheatgrass (*Agropyron desertorum* (Fisch.) Schult.), and western wheatgrass (*Agropyron smithii* Rydb.). Other cool season turfgrasses include beachgrass (*Ammophila breviligulata* Fern.), smooth bromegrass (*Bromus inermis* Leyss.), cattails such as Timothy (*Phleum pratense* L.), sand cattail (*Phleum subulatum* L.), orchardgrass (*Dactylis glomerata* L.), weeping alkaligrass (*Puccinellia distans* (L.) Parl.) and crested dog's-tail (*Cynosurus cristatus* L.).

Examples of warm season turfgrasses include Bermudagrass (*Cynodon* spp. L. C. Rich), zoysiagrass (*Zoysia* spp. Willd.), St. Augustine grass (*Stenotaphrum secundatum* Walt Kuntze), centipedegrass (*Eremochloa ophiuroides* Munro Hack.), carpetgrass (*Axonopus affinis* Chase), Bahia grass (*Paspalum notatum* Flugge), Kikuyugrass (*Pennisetum clandestinum* Hochst. ex Chiov.), buffalo grass (*Buchloe dactyloids* (Nutt.) Engelm.), Blue gramma (*Bouteloua gracilis* (H.B.K.) Lag. ex Griffiths), seashore paspalum (*Paspalum vaginatum* Swartz) and sideoats grama (*Bouteloua curtipendula* (Michx. Torr.). St. Augustine grass and Bermudagrass are the most preferred.

The following examples further illustrate details for the preparation and use of the compositions of this invention. The invention, which is set forth in the foregoing disclosure, is not to be limited either in spirit or scope by these examples. Those skilled in the art will readily understand that known variations of the conditions and processes of the following preparative procedures can be used to prepare these compositions.

EXAMPLES

Example 1

The products Allectus™ GC Granular and Allectus™ GC SC were created by making a formulation of imidacloprid and bifenthrin. The products were made as a granular formulation and a suspension concentrate, respectively, by methods known to those of skill in the art.

Example 2

The following test was performed to show the effectiveness of Example 1 on chinch bugs. The formulations tested were the soluble concentrate of Allectus GC SC product described in Example 1. FIG. 1 shows the results. The residual control obtained from the coformulation at doses resulting in application of 89 g/ha of bifenthrin plus 111 g/ha of imidacloprid, and of 133 g bifenthrin plus 167 g/ha imidacloprid is comparable to the control obtained with 222 g/ha of bifenthrin, and greatly superior to the control obtained with 330 g/ha of imidacloprid.

Example 3

The following test was performed to show the effectiveness of Allectus GC Granulate on southern and tawny mole crickets. The crickets were large nymphs, whereas the normal application timing for topically applied mole cricket products is at peak egg hatch (i.e., two months earlier in the season than the date on which this study began. FIG. 2 shows the results. The level of control at 14 days after treatment provided by a granular formulation of the combination product in Example 1, applied at doses that deliver 222 g/ha of bifenthrin plus 278 g/ha imidacloprid and 178 g/ha bifenthrin plus 222 g/ha imidacloprid, provided mole cricket control greatly superior to 222 g/ha of bifenthrin or by 450 g/ha imidacloprid, as measured on a non-linear 0-9 grid scale.

Example 4

The following tests were performed to show the efficacy of combinations containing imidacloprid and bifenthrin against pyrethroid-resistant chinch bugs (*Blissus hirsutus*).
Florida Study (a)
St. Augustine grass lawns, were treated in the summer of 2005 with either bifenthrin at 0.2 lb/A (220 g/ha) or with one of two combination products containing imidacloprid at 0.25 lb/A (280 g/ha) plus bifenthrin at 0.2 lb/A (220 g/ha). At the time of application, populations of chinch bugs were very low. The grass was irrigated and mowed according to local agronomic practices. Because of poor efficacy, imidacloprid is not used commercially for this application and thus was not tested alone in this study.

The numbers of chinch bugs in the lawns were counted at 40 days after application (DAT). After this time period, lawns treated with the combination products containing imidacloprid and bifenthrin had no chinch bugs. In contrast, chinch bug numbers in lawns treated with bifenthrin alone were at economically damaging levels. As a result, the lawns that were originally treated with bifenthrin alone were retreated with a foliar spray of imidacloprid (at 0.25 lb/A (280 g/ha) plus bifenthrin (at 0.2 lb/A (220 g/ha)). Twenty days after this second application to the first set of lawns, all the lawns were sampled again and no chinch bugs were detected. Periodic sampling of all treated lawns was done until October. Chinch bug populations in all lawns treated with imidacloprid plus bifenthrin remained very low for the duration of the study.

lawns was observed. A sample of these chinch bugs was collected and sent to the University of Florida, where a laboratory bioassay showed that the bugs were 47 times less susceptible to bifenthrin than a normal pyrethroid-susceptible population.

In October of 2005 the lawns were sampled, and the average population of chinch bugs in each lawn was 571 bugs/ft$^2$ (i.e., 571 bugs per about 930 cm$^2$), an exceedingly heavy population. After this sampling was done, the seven lawns were treated with a soluble concentrate formulation of a product containing imidacloprid plus bifenthrin at 0.25 lb/A plus 0.2 lb/A (280 g/ha plus 220 g/ha). Six days after treatment, the lawns were again sampled, at which time an average of 6 chinch bugs/ft$^2$ (i.e., 6 bugs per about 930 cm$^2$) was observed. This dramatic reduction in population demonstrates that the combination of imidacloprid and bifenthrin was very efficacious against chinch bugs that could not be controlled with bifenthrin alone.

Example 5

The following tests were performed to show the efficacy of combinations containing imidacloprid and bifenthrin against Japanese beetle eggs (*Popillia japonica*).

Turfgrass cores (6.4 cm in diameter, 7 cm deep) were set into tight-fitting paper cups. Four cores were arranged in an ABAB layout in cylindrical plastic cages (60 cm in diameter, 50 cm high) cages with lids that prevented any insects inside from escaping. The cages were sufficiently large to allow adult Japanese beetles to fly and/or crawl unimpeded from one core to another, thereby providing an experimental design that was an accurate measure of which type of turf (untreated or insecticide treated) the adult beetles preferred.

Tests were carried out using the following compositions compared to untreated controls:
Composition (1): Imidacloprid at 0.25 lb/A (about 280 g/ha) plus bifenthrin at 0.2 lb/A (about 220 g/ha)
Composition (2): Imidacloprid at 0.3 lb/A (about 340 g/ha)

Eight replicates of each paired comparison were tested. Gravid adult female Japanese beetles were collected from the field and eight females were placed in each cage. Tests were

| Test | Treatment | Product | Product applied | Imidacloprid applied | Bifenthrin applied | number of southern chinch bugs per ft$^2$ (per 930 cm$^2$) | | | | |
|---|---|---|---|---|---|---|---|---|---|---|
| | | | | | | 0 DAT | 40 DAT | 60 DAT | 100 DAT | 113 DAT |
| 1 | Bifenthrin | 0.1% on fertilizer | 175 lb/A (196 kg/ha) | — | 0.2 lb/A (220 g/ha) | 0 | 250 | — | — | — |
| | Imidacloprid + bifenthrin (applied 40 DAT) | 5% + 4% soluble conc. | 4.5 pt/A (5.3 L/ha) | 0.25 lb/A (280 g/ha) | 0.2 lb/A (220 g/ha) | — | — | 0 | 0 | 0 |
| 2 | Imidacloprid + bifenthrin | 0.1% + 0.08% on fertilizer | 175 lb/A (196 kg/ha) | 0.25 lb/A (280 g/ha) | 0.2 lb/A (220 kg/ha) | 0 | 0 | 0 | 3 | 2 |
| 3 | Imidacloprid + bifenthrin | 0.2% + 0.16% on clay | 87 lb/A (98 kg/ha) | 0.25 lb/A (280 g/ha) | 0.2 lb/A (220 g/ha) | 0 | 0 | 0 | 6 | 0 |

The data demonstrate that the combination of imidacloprid and bifenthrin provided excellent control of southern chinch bugs on lawns where bifenthrin alone was not effective.
Florida Study (b)
Seven St. Augustine grass lawns were treated several times in the summer of 2005 with bifenthrin at 0.2 lb/A (220 g/ha), the highest registered dose of the most widely-used product used for control of southern chinch bugs in Florida. Control was exceedingly poor and significant injury to the treated carried out at 25° C. and with 14 h photophase. One day after infestation, a piece of apple was added to the cage as a food/water source.

At 4 days after infestation, the numbers of adult beetles found in treated and untreated cores were counted. Results showed that only 2.5 beetles were found in cores treated with imidacloprid plus bifenthrin, as compared with 5.5 beetles in the untreated cores. This difference was statistically-significant at $P<0.05$. In contrast, 3.8 beetles were found in cores treated only with imidacloprid, as compared with 4.2 beetles in the untreated cores. The results from the two comparisons indicate that beetles avoid turf that is treated with the combination of the two active ingredients, whereas the beetles show preference when given a choice between imidacloprid-treated and untreated turf.

What is claimed is:

1. A method of controlling insect pests in turfgrass comprising applying a composition comprising a synergistically effective amount of imidacloprid and bifenthrin to turf that is susceptible to damage by insect pests, wherein said bifenthrin is applied at a rate from about 150 g/ha to 250 g/ha and said imidacloprid is applied at a rate from about 200 g/ha to about 350 g/ha.

2. A method of controlling surface feeding insect pests in turf grass in need of pest control comprising applying a composition comprising bifenthrin and imidacloprid at a rate at which one application of the composition provides control that is substantially biologically equivalent to 1.8 to 2.5 applications of bifenthrin when used alone at the same rate at which bifenthrin is used in the single application of the combination, and wherein said bifenthrin is applied at a rate from about 150 g/ha to 250 g/ha and said imidacloprid is applied at a rate from about 200 g/ha to about 350 g/ha.

3. The method of claim 1 wherein the insect pest is a surface feeding insect.

4. The method of claim 1 wherein the insect pest is a chinch bug.

5. The method of claim 1 wherein said bifenthrin is applied at a rate of about 220 g/ha.

6. The method of claim 1 wherein said imidacloprid is applied at a rate of about 280 g/ha.

7. The method of claim 1 wherein the insect pest is a mole cricket.

8. The method of claim 1 wherein the insect pest is a Japanese beetle.

* * * * *